United States Patent [19]

Palmer et al.

[11] Patent Number: 5,034,214

[45] Date of Patent: * Jul. 23, 1991

[54] SWEETNESS INHIBITOR FOR PHARMACEUTICAL PREPARATIONS AND PROCESS FOR PREPARATION

[75] Inventors: Marcia D. Palmer, Nanuet; Gary L. Hickernell, Ossining; Paul R. Zanno, Nanuet, all of N.Y.

[73] Assignee: Kraft General Foods, Inc., Glenview, Ill.

[*] Notice: The portion of the term of this patent subsequent to Feb. 12, 2008 has been disclaimed.

[21] Appl. No.: 601,978

[22] Filed: Oct. 4, 1990

Related U.S. Application Data

[62] Division of Ser. No. 752,212, Jul. 3, 1985, Pat. No. 4,992,279.

[51] Int. Cl.$^5$ ................................................ A61K 7/16
[52] U.S. Cl. ......................................... 424/56; 424/49; 514/772; 514/779; 514/783
[58] Field of Search ................... 424/56, 49; 514/772, 514/779, 783

[56] References Cited

U.S. PATENT DOCUMENTS 3,930,026 12/1975 Clark .................................. 426/3
4,992,279 2/1991 Palmer et al. ...................... 426/3

FOREIGN PATENT DOCUMENTS 1467790 12/1968 Fed. Rep. of Germany ........ 426/56

OTHER PUBLICATIONS

Moncrieff, The Chemical Senses, 1944, Leonard Hill: London, p. 72.

*Primary Examiner*—Joseph Golian
*Attorney, Agent, or Firm*—Linn I. Grim

[57] ABSTRACT

A sweetness inhibited pharmaceutical product and a process for inhibiting sweetness is disclosed. In this product and process an effective sweetness inhibiting amount of a compound selected from the group consisting of an alkali metal heptyl sulfonate, an alkaline earth metal heptyl sulfonate, an alkali metal octyl sulfonate, an alkaline earth metal octyl sulfonate and mixtures thereof is added to an ingestible composition to which a sweetener has been added.

18 Claims, No Drawings

SWEETNESS INHIBITOR FOR PHARMACEUTICAL PREPARATIONS AND PROCESS FOR PREPARATION

This is a division of application Ser. No. 06/752,212, filed 7/03/85, now U.S. Pat. No. 4,992,279 issued Feb. 12, 1991.

BACKGROUND OF THE DISCLOSURE

1. Field of the Invention

The present invention is directed to a sweetness modifier. More particularly, the present invention is directed to a sweetness inhibitor, said sweetness inhibitor comprising a sweetness inhibiting amount of a compound selected from the group consisting of an alkali metal heptyl sulfonate, an alkaline earth metal heptyl sulfonate, an alkali metal octyl sulfonate, an alkaline earth metal octyl sulfonate and mixtures thereof.

2. Background of the Prior Art

Sweetness is one of the primary taste cravings of both animals and humans Thus, the utilization of sweetening agents in foods in order to satisfy this sensory desire is well established. However, oftentimes sweetening agents are used in foods to provide functions other than sweetening. For example, sweetening agents can be utilized in foods as fillers, bulking agents, antimicrobial agents, freezing point depressants, stabilizers and the like.

In many instances, the utilization of a sweetening agent for purposes other than sweetening results in an excessively sweet taste. In those instances a modification of the formulation to reduce the sweetener level is required. This modification must, of course, occur without the concurrent reduction in the amount of sweetener utilized. Obviously, the sweetness level was incorporated to provide an additional function. Decrease in the sweetener will adversely effect this requirement.

One solution to this problem, known in the art, is the addition of a bitter or an acidic ingredient to the ingestible product to reduce sweetness perception. This solution has met with very little success in that the resultant ingestible product has an undesirable bitter or acidic taste.

Accordingly, in view of the above remarks it becomes readily apparent that it would be highly desirable to provide a sweetness inhibiting agent which, when added to ingestible compositions which are sweetened with naturally occurring, artificial or combinations of natural and artificial sweeteners, greatly reduce or eliminate unwanted or unpleasant sweet tastes thereby increasing the palatability of overly sweet products.

Alkyl sulfonates and salts thereof are known in the art. However, their utility has generally been limited to detergents and surfactants. Indeed, use of alkyl sulfonates as detergents and surfactants is usually restricted to alkyls of at least 10 to 12 carbon atoms. The use of alkyl sulfonate salts of any number of carbon atoms as sweetness inhibitors is unknown in the art.

SUMMARY OF THE INVENTION

It has now been discovered that alkali metal and alkaline earth metal salts of heptyl sulfonate and octyl sulfonate provide extraordinary inhibition of sweetness without alteration of the level of sweetener actually present in an ingestible product.

In accordance with the instant invention a process is provided for inhibiting sweetness in ingestible products which comprises adding an effective sweetness inhibiting amount of a compound selected from the group consisting of an alkali metal heptyl sulfonate, an alkaline earth metal heptyl sulfonate, an alkali metal octyl sulfonate, an alkaline earth metal octyl sulfonate and mixtures thereof to a sweetened ingestible composition.

DETAILED DESCRIPTION

The instant invention is directed to sweetness inhibition. In particular, the present invention is directed to the addition of an effective sweetness inhibiting amount of a sweetness inhibitor added to a sweetened ingestible product. This addition decreases sweetness perception.

The sweetness inhibitors within the contemplation of the present invention include alkali metal heptyl sulfonates, alkaline earth metal heptyl sulfonates, alkali metal octyl sulfonates, alkaline earth metal octyl sulfonates and mixtures thereof.

More preferably, the sweetness inhibitors of the present invention are sodium heptyl sulfonate, potassium heptyl sulfonate, calcium heptyl sulfonate, magnesium heptyl sulfonate, lithium heptyl sulfonate, sodium octyl sulfonate, potassium octyl sulfonate, calcium octyl sulfonate, magnesium octyl sulfonate, lithium octyl sulfonate and mixtures thereof.

Still more preferably, the sweetness inhibitors of the instant invention are sodium heptyl sulfonate, potassium heptyl sulfonate, sodium octyl sulfonate, potassium octyl sulfonate and mixtures thereof.

Most preferably, the sweetness inhibitors of the present invention are sodium heptyl sulfonate, sodium octyl sulfonate and mixtures thereof.

The sweetness inhibitor of the present invention may be used in conjunction with any of a number of known natural and/or artificial sweeteners including, for example, sucrose, fructose, corn syrup solids, high fructose corn syrup, dextrose, xylitol, sorbitol, mannitol, acesulfam, thaumatin, invert sugar, saccharin, cyclamate, dihydrochalcone, hydrogenated glucose syrups, aspartame (L-aspartyl-L-phenylalanine methyl ester) and other dipeptides, glycyrrhizin, stevioside and the like.

The sweetness inhibitors of the present invention are added to ingestible compositions to produce ingestible products. For the purposes of this invention ingestible compositions are defined as foodstuffs and pharmaceutical products and preparations. Typical ingestible compositions, which include foodstuffs and pharmaceutical preparations, in which the sweetness inhibitors of the present invention may be used are, for example, beverages, (including soft drinks, carbonated beverages, ready to mix beverages and the like), infused foods (e.g. fruits and vegetables), sauces, condiments, salad dressings, fruit juices, syrups, desserts (including puddings, gelatin, baked goods and frozen desserts, such as ice creams and sherbets), icings and fillings, soft frozen products (such as soft frozen creams, soft frozen ice creams and yogurts, soft frozen toppings, such as dairy or non-dairy whipped toppings), confections, toothpaste, mouthwashes, chewing gum, intermediate moisture foods, (e.g. rice and dog foods) and the like.

It is an aspect of the present invention that the sweetness inhibitors of the present invention eliminate perceived sweetness without substantially contributing a bitter, salty or sour taste of their own. That is, the inhibiting of sweet taste of a food product by the sweetness inhibitors of the present invention is not due to any taste inparted by the compound(s) which constitutes the sweetness inhibitor(s). Rather, sweetness inhibition is due to an unexpected and highly surprising effect which results when the sweetness inhibitor is combined with a sweetener in the food product and tasted by the consumer.

Accordingly, the discovery of the present invention resides in the utilization of very small quantities of the inhibiting compounds of this invention which reduce or even eliminate undesirable sweet and/or lingering aftertastes of sweetness imparted by ingestible products containing natural and/or artificial sweeteners without effecting the other desirable tastes and properties of the ingestible foodstuff or pharmaceutical product.

The versatility of the inhibitor compound of the present invention in the formulation of food products and pharmaceutical preparations is manifested in several ways. For example, the inhibitors can be added to an undesirably sweet product, for example, an overly sweet soft frozen product or infused vegetable product to reduce or eliminate the undesirable sweet taste but maintain the necessary soft, frozen or infusion properties of the product. On the other hand, the inhibitors can be incorporated into products in conjunction with added amounts of sweetener in order to form novel soft frozen products.

In order to achieve the inhibiting results of the present invention, the sweetness inhibiting compounds described above are generally added to a foodstuff or pharmaceutical product containing a sweetener at a level which is effective to inhibit sweetness perception of that product. More particularly, it is found that the results provided by the present invention occur when the inhibiting agent is added to the product (containing a sweetener) in an amount in the range of from about 0.005 to about 1.0 percent by weight. It is noted that greater concentrations of inhibitor are operable but not practical. Preferred concentrations of the sweetness inhibitors of the present invention are in the range of from about 0.05 percent to about 0.5 percent by weight. Most preferably, the sweetness inhibitor of this invention is present in a concentration of from about 0.3 percent to about 0.1 percent by weight. It is emphasized that the above-recited concentrations are based on the total weight of the foodstuff or pharmaceutical product.

The sweetness content of foodstuffs and pharmaceuticals to which the inhibitors of the present invention may be added to inhibit sweetness, in general, may be in the range of between 1 percent to about 50 percent sucrose equivalency. Generally, the inhibiting effect provided by the compounds of the present invention is experienced over a wide range of acidity, e.g. pH of 2 to 10, preferably a pH of 3 to 7.5, in buffered or unbuffered formulations.

A reduction of perceived sweetness of between 1% and 100% is achieved depending upon the particular ingestible product, the amount and kind of sweetener contained therein and concomitant amount of inhibitor employed.

The following examples are given to illustrate the instant invention. Since these examples are given for illustrative purposes only they should not be interpreted as limiting the invention in any way.

EXAMPLE 1

The Test Procedure

A taste panel was assembled. Members of the panel sipped, but did not swallow, various aqueous solutions. After tasting a sample panel members rinsed to remove any residual taste sensation before tasting the next sample. The panel members matched the sweetness of each of the aqueous solutions presented to them, with sucrose standards whose concentration ranged from 1 to 25% by weight. The panel members were not informed of the identity of the aqueous solutions. Upon correlation of the ratings, sweetness inhibiting effects of the inhibitors were statistically calculated.

EXAMPLE 2

Testing of Heptyl Sodium Sulfonate

A series of aqueous solutions of sucrose with and without the addition of heptyl sodium sulfonate were prepared It is noted that among the "sucrose solutions" without heptyl sodium sulfonate was the limiting case where the sucrose concentration was zero.

These samples were tested by the testing panel in accordance with procedure enumerated in Example 1. Upon correlation of the sweetness ratings reported by panel members, sweetness inhibition was manifested in terms of equivalent sucrose concentration. That is, the sweetness inhibiting effect of heptyl sodium sulfonate was reported as the decrease in sweetness from a sweetness of 5, 10 or 25 percent by weight aqueous sucrose solution. For example, a 5 percent sucrose solution to which 0.1 percent by weight heptyl sodium sulfonate was added obtained the same statistical average sweetness rating from the tasting panel as that obtained by a 4.0 percent by weight aqueous sucrose solution.

Complete results of this tested are reported below in Table I. It is noted that all test samples were carefully controlled in terms of their acidity. The acidity of each solution is therefore reported. In all cases, comparisons were based on samples having the same acidity.

TABLE I

| Conc. of Heptyl Sodium Sulfonate, % by weight | Sucrose Conc. of Aqueous Solution to which Sulfonate was added, % by wt. | Concentration of Equiv. Aqueous Sucrose Solution, % by weight | pH |
|---|---|---|---|
| 0.0 | 5 | 4.5 | 7 |
| 0.1 | 5 | 4.0 | 7 |
| 0.2 | 5 | 3.0 | 7 |
| 0.3 | 5 | 1.5 | 7 |
| 0.5 | 5 | 1.0 | 7 |
| 0.0 | 10 | 11 | 7 |
| 0.1 | 10 | 9 | 7 |
| 0.2 | 10 | 6.5 | 7 |
| 0.3 | 10 | 4.5 | 7 |
| 0.5 | 10 | 4 | 7 |
| 0.0 | 25 | 20 | 7 |
| 0.1 | 25 | 20 | 7 |
| 0.2 | 25 | 17.5 | 7 |
| 0.3 | 25 | 13 | 7 |
| 0.5 | 25 | 10 | 7 |

EXAMPLE 3

Testing of Octyl Sodium Sulfonate

Example 2 was repeated but for the substitution of octyl sodium sulfonate for heptyl sodium sulfonate as sweetness inhibitor. The results of this experiment are summarized in Table II.

TABLE II

| Conc. of Octyl Sodium Sulfonate, % by weight | Sucrose Conc. of Aqueous Solution to which Sulfonate was added, % by wt. | Concentration of Equiv. Aqueous Sucrose Solution, % by weight | pH |
|---|---|---|---|
| 0.0 | 5 | 5.5 | 7 |
| 0.1 | 5 | 3.5 | 7 |
| 0.2 | 5 | 1 | 7 |

TABLE II-continued

| Conc. of Octyl Sodium Sulfonate, % by weight | Sucrose Conc. of Aqueous Solution to which Sulfonate was added, % by wt. | Concentration of Equiv. Aqueous Sucrose Solution, % by weight | pH |
|---|---|---|---|
| 0.3 | 5 | <1 | 7 |
| 0.5 | 5 | <1 | 7 |
| 0.0 | 10 | 12 | 7 |
| 0.1 | 10 | 7 | 7 |
| 0.2 | 10 | 5.5 | 7 |
| 0.3 | 10 | 3 | 7 |
| 0.3 | 10 | 2 | 7 |
| 0.5 | 10 | 1.5 | 7 |
| 0.0 | 25 | 25 | 7 |
| 0.1 | 25 | 20 | 7 |
| 0.2 | 25 | 15 | 7 |
| 0.3 | 25 | 11.5 | 7 |
| 0.5 | 25 | 9 | 7 |

DISCUSSION OF THE RESULTS

Tables I and II, summarizing the data of Examples 2 and 3 respectively, establish the sweetness inhibiting effect of the sweetness inhibitors of the present invention. Under neutral (pH of 7) conditions a minimum of 10% up to a maximum of approximate 85% decrease in sweetness perception was obtained employing the two preferred sweetness inhibitors of the present invention, heptyl sodium sulfonate and octyl sodium sulfonate.

The above preferred embodiments and examples are provided to illustrate the scope and spirit of the instant invention. These embodiments and examples will make apparent, to those skilled in the art, other embodiments and examples within the scope and spirit of this invention. These other embodiments and examples are within the contemplation of the present invention. Therefore, the scope of the instant invention should be limited only by the appended claims.

What is claimed is:

1. A process for inhibiting sweetness in pharmaceutical preparations comprising adding, to a pharmaceutical preparation containing a sweetener, an effective sweetness inhibiting amount of a compound selected from the group consisting of an alkali metal heptyl sulfonate, an alkaline earth metal heptyl sulfonate, an alkali metal octyl sulfonate, an alkaline earth octyl sulfonate and mixtures thereof, said sweetness inhibitin compound is present in a concentration in the range of between about 0.005 and 1.0 percent by weight, based on the total weight of the ingestible product, and said sweetener is present in the range between 1 percent to about 50 percent sucrose equivalency.

2. A process in accordance with claim 1 wherien said compound is selected from the group consisting of sodium heptyl sulfonate, potassium heptyl sulfonate, calcium heptyl sulfonate, magnesium heptyl sulfonate, lithium heptyl sulfonate, sodium octyl sulfonate, potassium octyl sulfonate, calcium octyl sulfonate, magnesium octyl sulfonate, lithium octyl sulfonate and mixtures thereof.

3. A process in accordance with claim 2 wherein said compound is selected from the group consistinf of sodium hepty sulfonate, potassium heptyl sulfonate, sodium octyl sulfonate, potassium octyl sulfonate and mixtures thereof.

4. A process in accordance with claim 3 wherein said compound is selected from the group consisting of sodium heptyl sulfonate, sodium octyl sulfonate and mixtures thereof.

5. A process in accordance with claim 1 wherein said compound is present in a concentration in the range of between about 0.05 and 0.5 percent by weight, based on the total weight of the pharmaceutical preparation.

6. A process in accordance with claim 5 wherein said compound is present in a concentration in the range of between 0.1 and 0.5 percent by weight, based on the total weight of the pharmaceutical preparation.

7. A process in accordance with claim 1 wherein said sweetener is selected from the group consisting of sucrose, fructose, corn syrup solids, high fructose corn syrup, dextrose, xylitol, sorbitol, mannitol, acesulfam, thaumatin, invert sugar, saccharin, cyclamate, dihydrochalcone, hydrogenated glucose syrups, aspartame, glycyrrhizin, stevioside and mixtures thereof.

8. A process in accordance with claim 1 wherein asid pharmaceutical preparation is a toothpaste.

9. A process in accordance with claim 1 wherein said pharmaceutical preparation is a mouthwash.

10. A pharmaceutical preparation comprising a pharmaceutical preparation, a sweetener and a sweetness inhibitor, said inhibitor selected from the group consisting of an alkali metal heptyl sulfonate, an alkaline earth metal heptyl sufonate, an alkali metal octyl sulfonate, an alkaline earth metal octyl sulfonate and mixtures thereof, wherein said sweetness inhibitor is present in a concentration in the range of between about 0.005 and 1.0 percent by weight, based on the total weight of said ingestible product, and said sweetener present in the range between 1 percent to about 50 percent sucrose equivalency.

11. A pharmaceutical preparation in accordance with claim 10 wherein said inhibitor is selected from the group consisting of sodium heptyl sulfonate, potassium heptyl sulfonate, calcium heptyl sulfonate, magnesium heptyl sulfonate, lithium heptyl sulfonate, sodium octyl sulfonate, potassium octyl sulfonate, calcium octyl sulfonate, magnesium octyl sulfonate, lithium octyl sulfonate and mixtures thereof.

12. A pharmaceutical preparation in accordance with claim 11 wherein said inhibitor is selected from the group consisting of sodium heptyl sulfonate, potassium heptyl sulfonate, sodium octyl sulfonate, poatssium octyl sulfonate and mixtures thereof.

13. A pharmaceutical preparation in accordance with claim 12 wherein inhibitor is selected from the group consisting of sodium heptyl sulfonate, sodium octyl sulfonate and mixtures thereof.

14. A pharmaceutical preparation in accordance with claim 10 wherein sweetness inhibitor is present in a concentration in the range of between about 0.05 and 0.5 percent by weight, based on the total weight of said ingestible product.

15. A pharmaceutical preparation in accordance with claim 14 wherein said sweetness inhibitor is present in a concentration in the range of between about 0.1 and 0.5 percent by weight, based on the total weight of said ingestible product.

16. A pharmaceutical preparation in accordance with claim 10 wherein said sweetener is selected from the group consisting of sucrose, fructose, corn syrup solids, high fructose corn syrup, dextrose, xylitol, sorbitol, mannitol, acesulfam, dihydrochalcone, hydrogenated glucose syrups, aspartame, glycyrrhizin, stevioside and mixtures thereof.

17. A pharmaceutical preparation in accordance with claim 10 wherein said preparation is a toothpaste.

18. A pharmaceutical preparation in accordance with claim 10 wherein said preparation is a mouthwash.

* * * * *